United States Patent
Yang et al.

(10) Patent No.: US 8,953,155 B1
(45) Date of Patent: Feb. 10, 2015

(54) OPTICAL INSPECTION SYSTEM AND OPTICAL INSPECTION METHOD

(71) Applicant: Taiwan Semiconductor Manufacturing Co., Ltd, Hsin-Chu (TW)

(72) Inventors: Tai-I Yang, Hsinchu (TW); Hong-Seng Shue, Zhubei (TW); Ming-Tai Chung, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 14/037,976

(22) Filed: Sep. 26, 2013

(51) Int. Cl.
*G01N 21/00* (2006.01)
*G01N 21/55* (2014.01)

(52) U.S. Cl.
CPC .................................. *G01N 21/55* (2013.01)
USPC .................................. 356/237.1; 356/237.2

(58) Field of Classification Search
USPC .......... 356/237.1–237.6, 239.1–239.8
See application file for complete search history.

(56) References Cited

U.S. PATENT DOCUMENTS

| | | | |
|---|---|---|---|
| 2003/0137655 A1* | 7/2003 | Wegmann | 356/124 |
| 2010/0195177 A1* | 8/2010 | Yoshinari et al. | 359/10 |
| 2013/0155400 A1* | 6/2013 | Nakao et al. | 356/237.2 |

FOREIGN PATENT DOCUMENTS

EP      1 292 361 B1    2/2008

* cited by examiner

*Primary Examiner* — Tri T Ton
(74) *Attorney, Agent, or Firm* — Birch, Stewart, Kolasch & Birch, LLP

(57) ABSTRACT

Embodiments of mechanisms of an optical inspection system for inspecting an object are provided. The optical inspection system includes a light source emitting a coherent beam having a first width, and a beam expander increasing the first width to a second width. The optical inspection system also includes a polaroid module adjacent to the beam expander and polarizing the coherent beam. The object generates an inspection beam with an interference pattern by reflecting the polarized coherent beam. The optical inspection system further includes an image module capturing the inspection beam.

19 Claims, 14 Drawing Sheets

OPTICAL INSPECTION SYSTEM AND OPTICAL INSPECTION METHOD

BACKGROUND

MEMS (Micro Electro Mechanical Systems) devices are used in a variety of electronic applications, such as personal computers, cell phones, digital cameras, and other electronic equipment. Because of the size of MEMS devices, the MEMS devices are usually inspected for defects by some specific microscopes, such as scanning electron microscopes (SEM), or atomic force microscopes (AFM). However, the SEM or the AFM inspect the MEMS devices by emitting electrons or atoms, and that will damage the MEMS devices.

Optical microscopes may be usually used for inspecting MEMS devices to prevent damage. However, the optical microscopes for MEMS devices have very complex and precise mechanisms, and therefore, the manufacturing of the optical microscopes is very difficult, and the manufacturing cost of the optical microscopes is very expensive. Moreover, the inspection processes of the microscopes are very complex and take a lot of time.

Therefore, there are challenges to the manufacturing of optical microscopes and improving the inspection methods of the optical microscopes.

BRIEF DESCRIPTION OF THE DRAWINGS

For a more complete understanding of the present disclosure, and the advantages of the present disclosure, reference is now made to the following descriptions taken in conjunction with the accompanying drawings, in which.

DETAILED DESCRIPTION

It is to be understood that the following disclosure provides many different embodiments, or examples, for implementing different features of the disclosure. Specific examples of components and arrangements are described below to simplify the present disclosure. These are, of course, merely examples and are not intended to be limiting. Moreover, the performance of a first process before a second process in the description that follows may include embodiments in which the second process is performed immediately after the first process, and may also include embodiments in which additional processes may be performed between the first and second processes. Various features may be arbitrarily drawn in different scales for the sake of simplicity and clarity. Furthermore, the formation of a first feature over or on a second feature in the description may include embodiments in which the first and second features are formed in direct or indirect contact.

Figure 1:
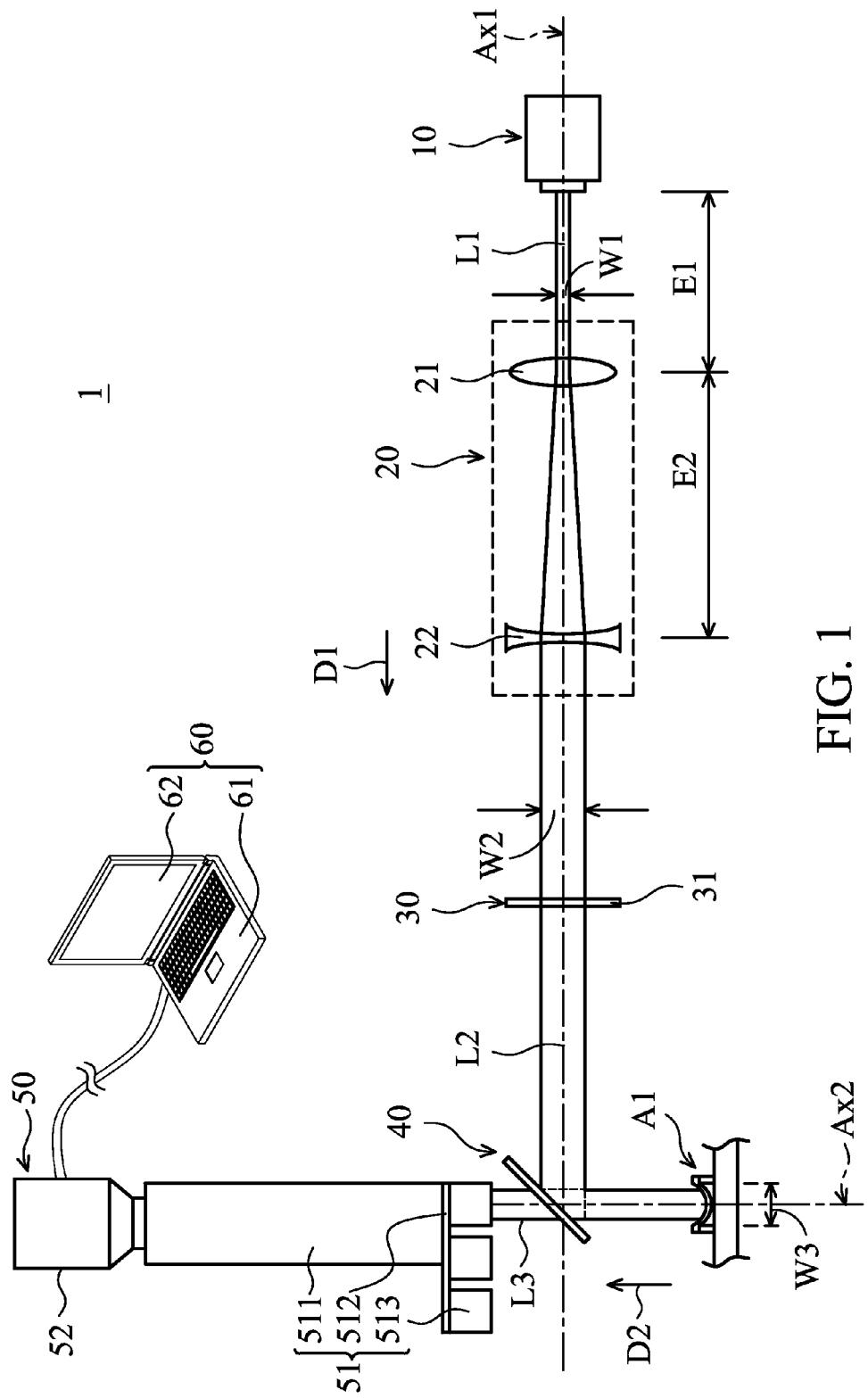
FIGS. 1 and 2 are schematic views of optical inspection systems in accordance with some embodiments of the disclosure.

FIG. 1 is a schematic view of an optical inspection system 1 in accordance with some embodiments of the disclosure. Optical inspection system 1 for inspecting an object A1 includes a light source 10, a beam expander 20, a polaroid module 30, a half-reflect mirror 40, an image module 50, and a computer 60. In some embodiments, light source 10, beam expander 20, polaroid module 30, and half-reflect mirror 40 are arranged along a first axis AX1, and object A1, half-reflect mirror 40, and image module 50 are arranged along a second axis AX2 in sequence. First axis AX1 is perpendicular to second axis AX2.

The arrangement of light source 10, beam expander 20, polaroid module 30, half-reflect mirror 40, image module 50, and computer 60 varies. In some embodiments, light source 10, beam expander 20, polaroid module 30, half-reflect mirror 40, and object A1 are arranged along first axis AX1 (or second axis AX2), and half-reflect mirror 40, and image module 50 are arranged along second axis AX2 (or first axis AX1) in sequence.

As shown in FIG. 1, light source 10 emits a light beam (coherent beam L1, polarized coherent beam L2, and inspection beam L3) which is transmitted to beam expander 20, polaroid module 30, half-reflect mirror 40, and object A1, and reflected by object A1. Next, after object A1 reflects the light beam, the reflected light beam is transmitted to half-reflect mirror 40 and image module 50, and captured by image module 50. In some embodiments, polarized coherent beam L2 emitted to object A1 and inspection beam L3 reflected by object A1 are transmitted along the same axis (second axis AX2).

In some embodiments, light source 10 is a coherent light source, such as a laser emitting device or coherent filtered light in same wavelength by photomultiplier amplifying. The laser emitting device may be a gas laser emitting device, a liquid laser emitting device, a solid state laser emitting device, or a semiconductor laser emitting device.

For example, light source 10 is a laser emitting device emitting a coherent beam L1, such as a laser beam along a first direction D1 and first axis AX1, and first direction D1 is parallel to first axis AX1. In some embodiments, coherent beam L1 has a single wavelength in a range from about 380 nm to about 700 nm, such as a monochromatic light. The energy of coherent beam L1 is in a range from about 3 mw to about 10 mw. For example, the wavelength of coherent beam L1 is about 532 nm, and the energy of coherent beam L1 is about 5 mw.

The beam expander 20 increases width W1 of coherent beam L1 to width W2, which is greater than width W1. Width W2 is substantially the same as or approaches to width W3 of object A1. In some embodiments, width W1 of coherent beam L1 is in a range from about 0.05 mm to about 0.2 mm. In some embodiments, width W2 of coherent beam L1 is in a range from about 0.4 mm to about 1 mm. In some embodiments, and width W3 of object A1 is in a range from about 0.4 mm to about 1 mm. For example, width W1 is about 0.1 mm, width W2 is about 0.5 mm, and width W3 is about 0.6 mm.

Beam expander 20 includes a first lens 21 and a second lens 22 arranged along first axis AX1 in sequence. First lens 21 is adjacent to light source 10, and second lens 22 is adjacent to polaroid module 30. First lens 21 is a symmetrical double convex lens, and second lens 22 is a symmetrical biconcave lens. The refractive index of first and second lenses 21 and 22 are in a range about 1.33 to 2.0. The first and second lenses 21 and 22 are made of glass.

Coherent beam L1 between first lens 21 and light source 10 is collimated light with constant width W1. After coherent beam L1 passes through first lens 21, the width of coherent beam L1 is gradually greater between first lens 21 and second lens 22. Further, after coherent beam L1 passes through second lens 22, coherent beam L1 has a constant width W2. Therefore, optical inspection system 1 adapts to the variety of sizes of object A1 by adjusting and modifying the lenses of beam expander 20.

In some embodiments, first lens 21 has a focal length in a range less than 20 cm, and a radius of curvature in a range less than 2 cm. In some embodiments, second lens 22 has a focal length in a range large than −20 cm, and a radius of curvature in a range large than 2 cm. In some embodiments, a distance E1 between light source 10 and first lens 21 equal to focal length of lens 21. In some embodiments, a distance E2 between first lens 21 and second lens 22 equal to absolute value of focal length of lens 22. For example, the first lens 21 has a focal length about 15 cm, and a radius of curvature about 1.32 cm. Second lens 22 has a focal length about −10 cm, and a radius of curvature about −0.82 cm. A distance E1 between light source 10 and first lens 21 is about 15 cm. A distance E2 between first lens 21 and second lens 22 is about 10 cm.

Polaroid module 30 is adjacent to beam expander 20, and transforms coherent beam L1 to a polarized coherent beam L2 transmitted along first direction D1 and first axis AX1. Polarized coherent beam L2 has a constant width, and the width of polarized coherent beam L2 is the same as width W2 of coherent beam L1. Further, polarized coherent beam L2 is polarized light, such as S-wave polarized light or S-wave polarized light, and collimated light. Polaroid module 30 includes a polaroid 31, such as a linear polaroid or a circular polaroid.

Half-reflect mirror 40 reflects polarized coherent beam L2 to object A1. Half-reflect mirror 40 is inclined about 45 degrees relative to first axis AX1 and second axis AX2. Therefore, polarized coherent beam L2 is transmitted along second axis AX2, which is perpendicular to first axis AX1, after being reflected by half-reflect mirror 40.

After polarized coherent beam L2 is emitted to object A1, object A1 generates an inspection beam L3 with an interference pattern by reflecting polarized coherent beam L2. Inspection beam L3 has a constant width, and the width of inspection beam L3 is the same as width W2 of coherent beam L1. Further, inspection beam L3 is transmitted along a second direction D2 and second axis AX2, and second direction D2 is parallel to second axis AX2. Further, inspection beam L3 passes through half-reflect mirror 40 to image module 50 along second direction D2 and second axis AX2.

Image module 50 includes a microscope 51 and a camera 52. Microscope 51 includes a microscope mechanism 511, a rotating element 512, and several lens elements 513. Rotating element 512 is pivoted on microscope mechanism 511, and lens elements 513 are fixed on rotating element 512. Each of lens elements 513 corresponds to the different widths of the objects, and one of lens elements 513 is aligned to inspection beam L3 and second axis AX2 by rotating the rotating element 512.

Camera 52 is disposed on microscope 51. Camera 52 may be a charge-coupled device. Computer 60 includes a processes module 61 and a display 62 electrically connected with processes module 61. Processes module 61 is communicated with camera 52 by wire or wireless network.

Inspection beam L3 passes through lens elements 513 and microscope mechanism 511 to camera 52 and is captured by camera 52. After camera 52 captures inspection beam L3, camera 52 generates an image signal according to the interference pattern of inspection beam L3 to processes module 61. Processes module 61 generates an inspection signal to display 62 according to image signal, and display 62 displays an inspection image according to the inspection signal.

Figure 2:
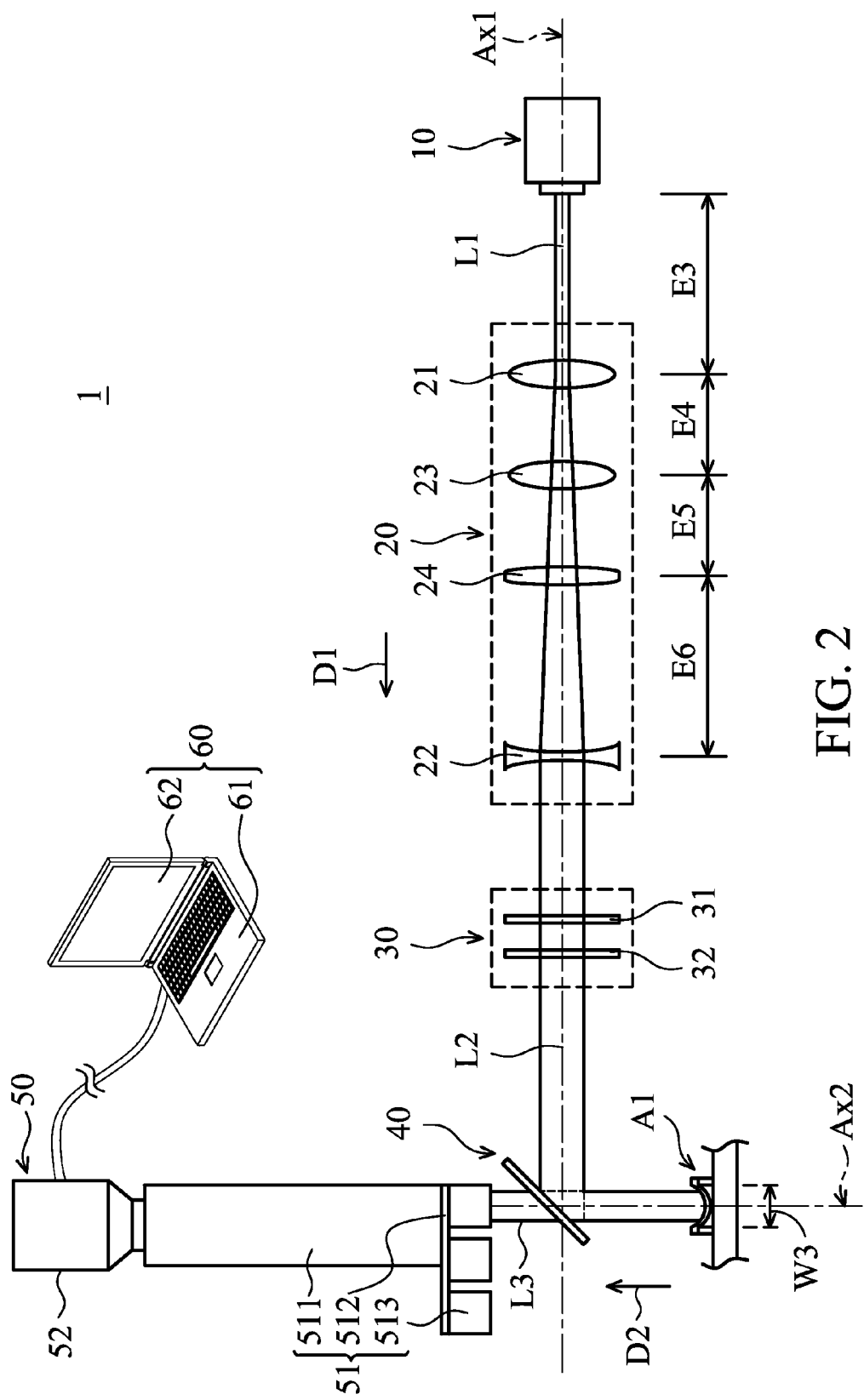

FIG. 2 is a schematic view of an optical inspection system in accordance with some embodiments of the disclosure. FIG. 2 is similar to FIG. 1, except that beam expander 20 further includes a third lens 23 and a fourth lens 24. As shown in FIG. 2, third lens 23 and fourth lens 24 are between first lens 21 and second lens 22, and first lens 21, third lens 23, fourth lens 24, and second lens 22 are arranged along first axis AX1 in sequence.

First lens 21, third lens 23, and fourth lens 24 are symmetrical double convex lenses. In some embodiments, as shown in FIG. 2, first lens 21 has a focal length in a range less than 10 cm, and a radius of curvature in a range less than 1.3 cm. In some embodiments, second lens 22 has a focal length in a range larger than −10 cm, and a radius of curvature in a range larger than −1.3 cm. In some embodiments, third lens 23 has a focal length in a range less than 10 cm, and a radius of curvature in a range less than 1.3 cm. In some embodiments, fourth lens 24 has a focal length in a range less than 20 cm, and a radius of curvature in a range less than 2 cm. For example, first lens 21 has a focal length about 3.5 cm, and a radius of curvature about 0.48 cm. Second lens 22 has a focal length about −10 cm, and a radius of curvature about −0.82 cm. Third lens 23 has a focal length about 4 cm, and a radius of curvature about 0.63 cm. Fourth lens 24 has a focal length about 15 cm, and a radius of curvature about 1.32 cm.

In some embodiments, a distance E3 between light source 10 and first lens 21 equal to focal length of first lens 21. In some embodiments, a distance E4 between first lens 21 and third lens 23 equal to focal length of third lens 23. In some embodiments, a distance E5 between third lens 23 and fourth lens 24 equal to focal length of lens 24, a distance E6 between fourth lens 24 and second lens 22 equal to absolute value of focal length of second lens 22. For, example, a distance E3 between light source 10 and first lens 21 is about 3.5 cm. A distance E4 between first lens 21 and third lens 23 is about 4 cm. A distance E5 between third lens 23 and fourth lens 24 is about 15 cm. A distance E6 between fourth lens 24 and second lens 22 is about 10 cm.

In addition, polaroid module 30 includes a first polaroid 31 and a second polaroid 32 arranged along a first axis AX1 in sequence and parallel to each other. In some embodiments, the structure of first polaroid 31 and second polaroid 32 are the same. Therefore, by first polaroid 31 and second polaroid 32, the polarization of polarized coherent beam L2 is improved.

As shown in FIGS. 1 and 2, the optical inspection system 1 of the present disclosure has a simplification structure, and therefore, the difficulty of the manufacturing and the manufacturing cost of the optical inspection system 1 are decreased.

Figure 3A:
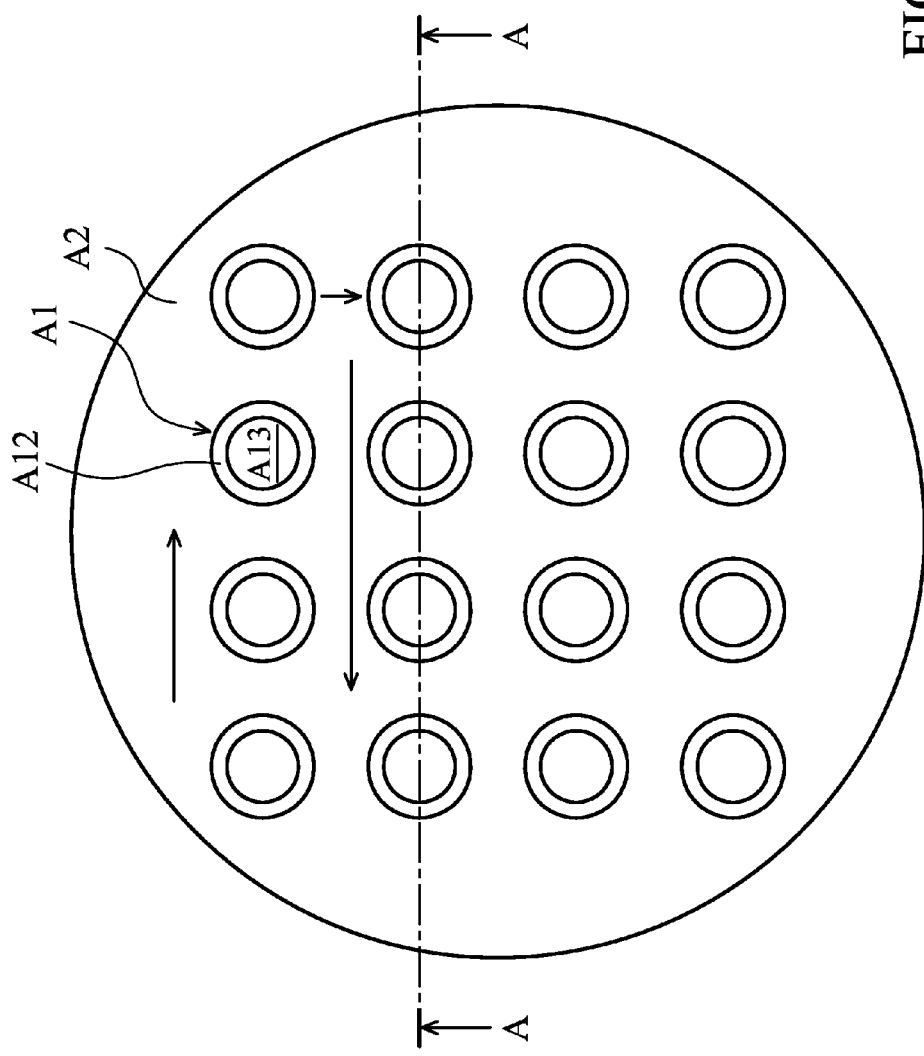
FIG. 3A is a top view of an object and a substrate in accordance with some embodiments of the disclosure.
Figure 3B:
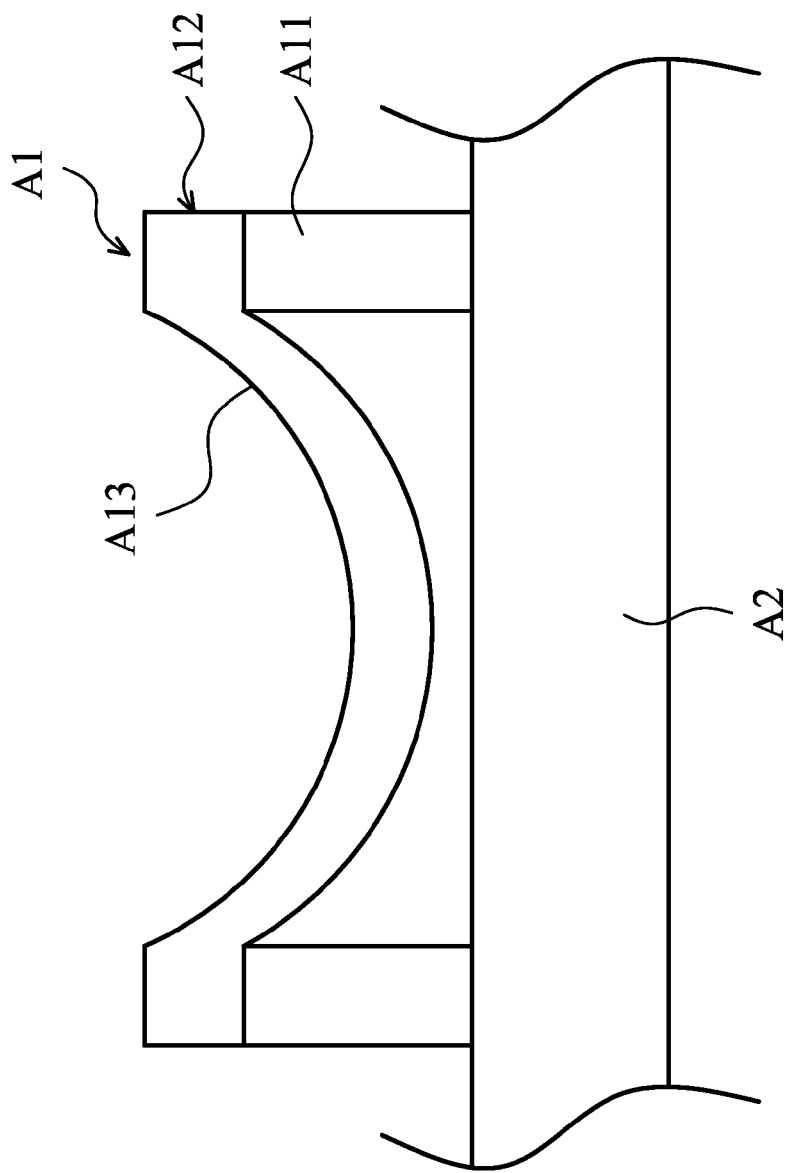
FIG. 3B is a cross-sectional view of the object and the substrate along line AA of FIG. 3A.

FIG. 3A is a top view of object A1 and substrate A2 in accordance with some embodiments of the disclosure. FIG. 3B is a cross-sectional view of object A1 and substrate A2 along line AA of FIG. 3A. Objects A1 are arranged on substrate A2 in array. Object A1 may be an MEMS (Micro Electro Mechanical Systems) element, and substrate A2 may be a wafer. In some embodiments, object A1 is a microphone including a support element A11 and a membrane A12 with a curved surface A13. Optical inspection system 1 inspects objects A1 in sequence.

Figure 4A:
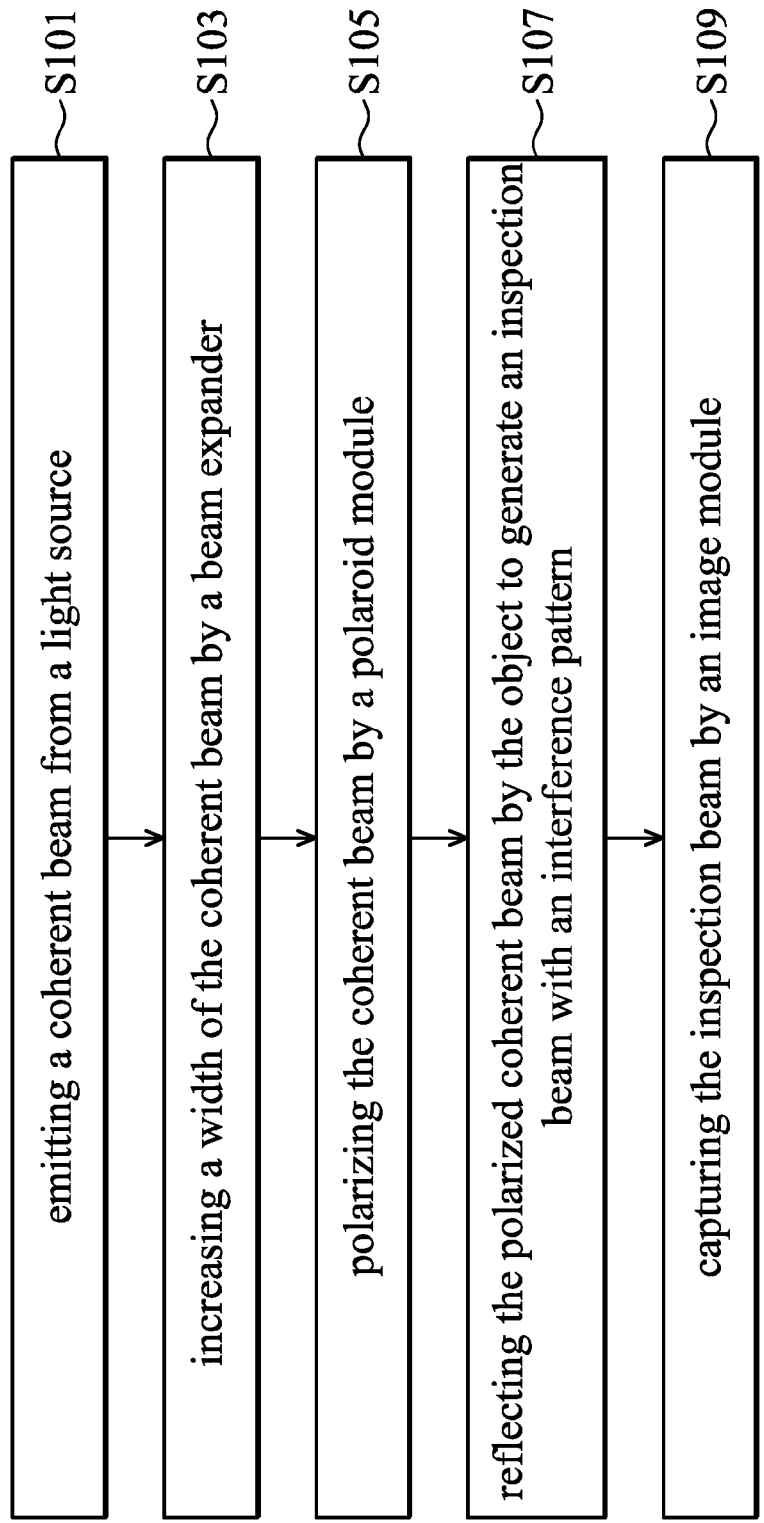
FIGS. 4A and 4B are flow charts of an optical inspection method in accordance with some embodiments of the disclosure.
Figure 4B:
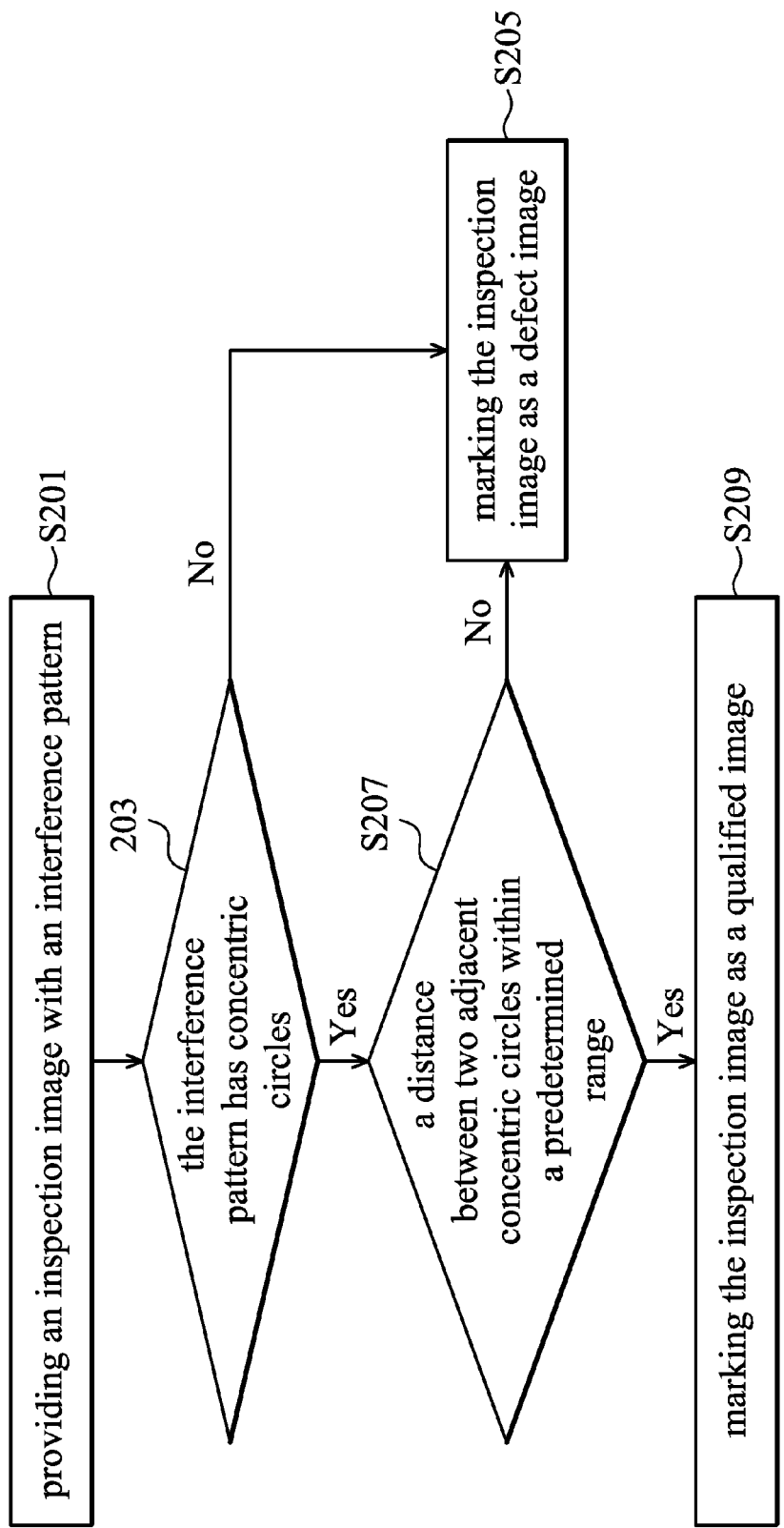
Figure 5:
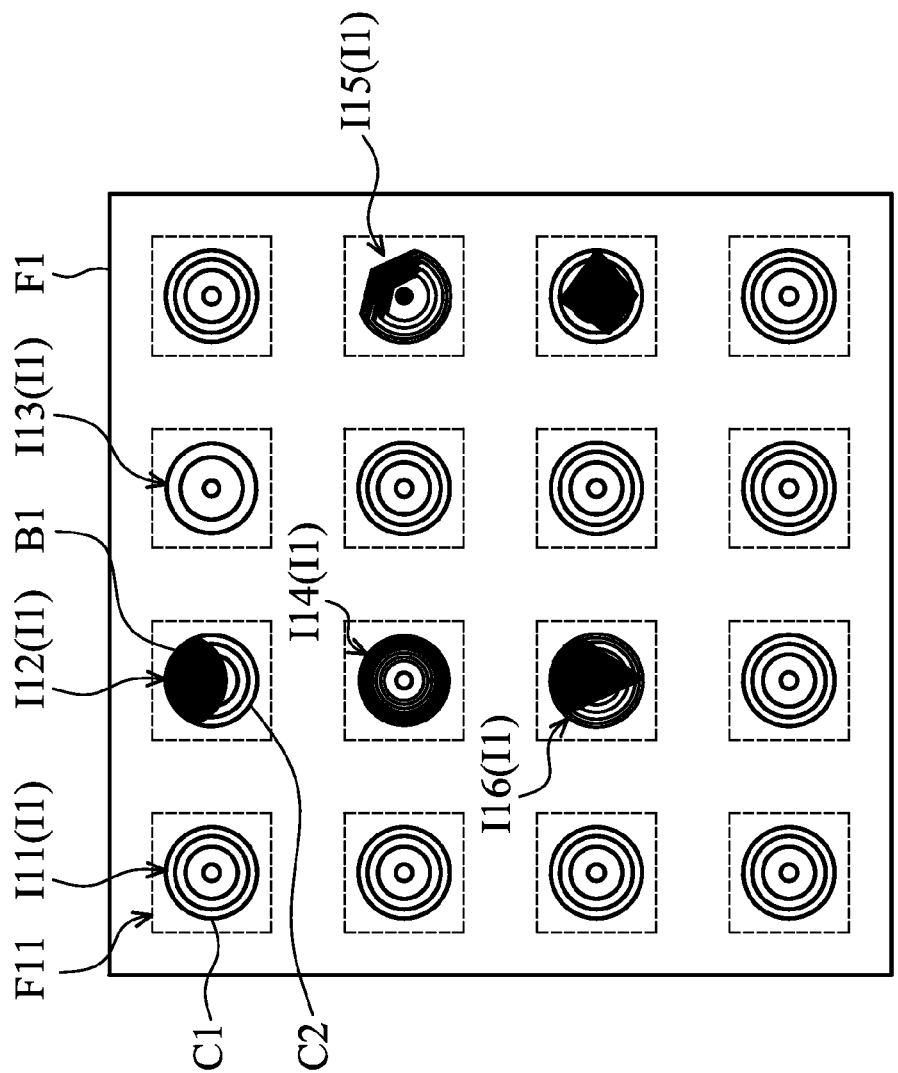
FIG. 5 is an image frame in accordance with some embodiments of the disclosure.

FIGS. 4A and 4B are flow charts of an optical inspection method in accordance with some embodiments of the disclosure. FIG. 5 is an image frame F1 in accordance with some embodiments of the disclosure. First, light source 10 emits coherent beam L1 (step S101). Next, width of coherent beam L1 is increased by coherent beam L1 passing through beam expander 20 (step S103), and coherent beam L1 is polarized by passing through polaroid module 30 (step S105). Polarized coherent beam L2 is reflected to object A1 by half-reflect mirror 40.

Polarized coherent beam L2 is reflected by object A1 to generate inspection beam L3 with an interference pattern (step S107). Next, inspection beam L3 passes through half-reflect mirror 40 to image module 50, and is captured by image module 50 (step S109). Repeating steps S101 to S109, optical inspection system 1 inspects each of objects A1 on substrate A2.

In some embodiments, polarized coherent beam L2 is emitted to object A1 by passing through half-reflect mirror 40, and inspection beam L3 is reflected to image module 50 by half-reflect mirror 40.

Further, image module 50 generates an image signal of each of objects A1 to processes module 61, and processes module 61 generates an inspection signal according to the image signal. Display 62 displays an image frame F1 according to the inspection signal. Image frame F1 includes inspection images F11 arranged thereon in array. Each of inspection images F11 has one interference pattern I1 corresponds one curved surface A13 of object A1 as shown in FIG. 3A (step 201).

Next, whether interference pattern I1 has concentric circles C1 is detected (step S203). If interference pattern I1 excludes concentric circles C1, inspection image F11 is marked as a defect image, and object A1 corresponding to inspection image F11 is classified as a defect object (step S205). As shown in FIG. 5, for example, interference patterns I1 include interference patterns I11, I12, I13, I14, I15 and I16 in varied types. Interference pattern I12 has a mass area B1 and curves C2. Therefore, interference pattern I12 excludes concentric circles C1, and object A1 corresponding to interference pattern I12 is classified as a defect object.

Further, whether a distance between two adjacent concentric circles C1 is within a predetermined range is detected (step S207). If the distance greater than the predetermined range, inspection image F11 in FIG. 5 is also marked as a defect inspection image, and object A1 corresponding to inspection image F11 is classified as a defect object (step S205). Further, if the distance is within the predetermined range, inspection image F11 is marked as a qualified image, and object A1 corresponding to inspection image F11 is classified as a qualified object (step S209).

For example, a distance between two adjacent concentric circles C1 of interference pattern I13 in FIG. 5 exceeds the predetermined range, and object A1 corresponding to interference pattern I13 is classified as a defect object. If a distance between two adjacent concentric circles C1 of interference pattern I11 is within the predetermined range, then object A1 corresponding to interference pattern I11 is classified as a qualified object.

As shown in FIG. 5, for example, interference patterns I12, I13, I14, I15 and I16 are defect interference patterns, which is significant difference from a qualified interference pattern I11. Therefore, the determination of an object A1 whether having defect is easier.

Figure 6A:
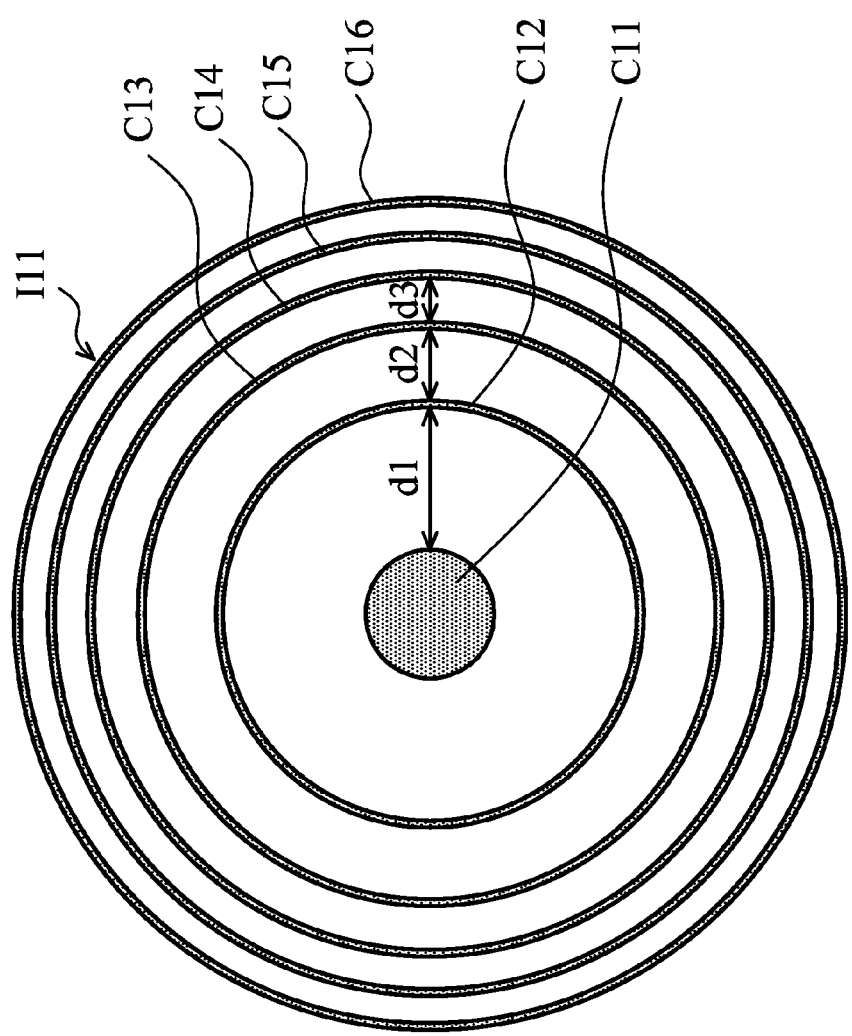
FIG. 6A is a top view of an interference pattern in accordance with some embodiments of the disclosure.
Figure 6B:
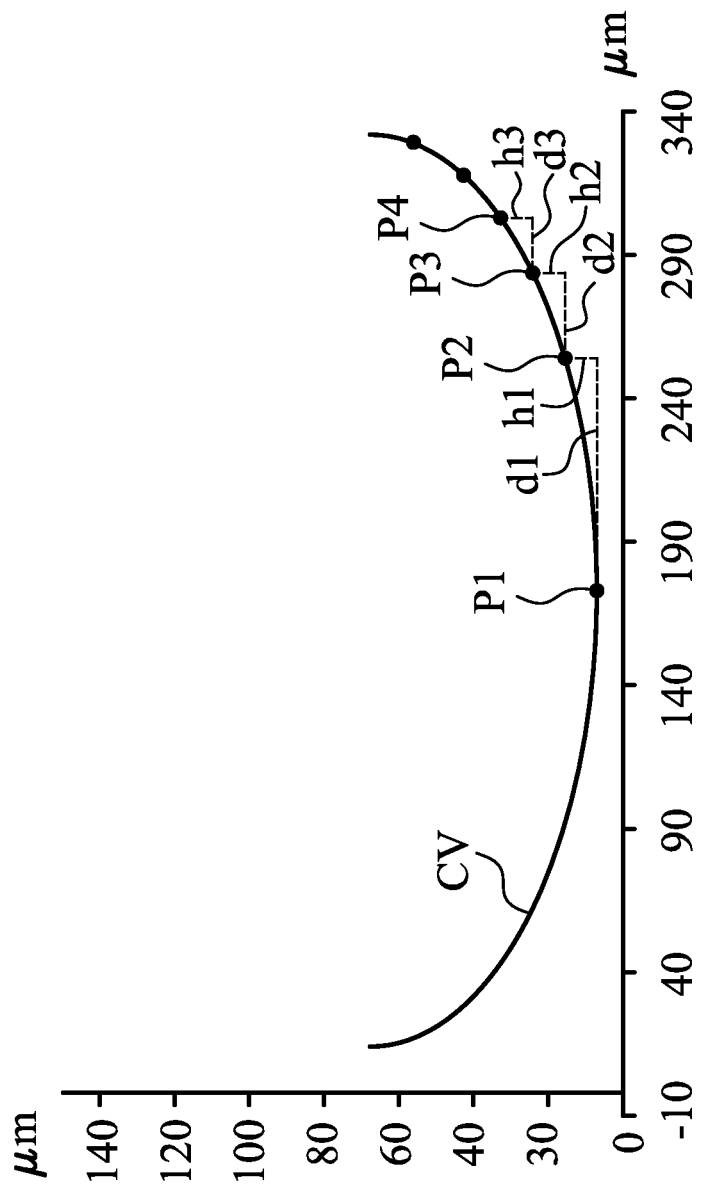
FIG. 6B is a curve diagram corresponding to the interference pattern in FIG. 6A.

FIG. 6A is a top view of an interference pattern I11 in accordance with some embodiments of the disclosure. FIG. 6B is a curve diagram corresponding to interference pattern I11 in FIG. 6A. As shown in FIGS. 6A and 6B, for example, interference pattern 111 has concentric circles C11, C12, C13, C14, C15, and C16. For example, a first distance d1 between concentric circles C11 and C12 is about 80 um, a second distance d2 between concentric circles C12 and C13 is about 30 um, and a third distance d3 between concentric circles C13 and C14 is about 15 um.

In addition, a first predetermined range corresponding to first distance d1 is in a range of from about 78 nm to about 82 nm, a second predetermined range corresponding to second distance d2 is in a range of from about 28 nm to about 32 nm, and a third predetermined range corresponding to third distance d3 is in a range of from about 13 nm to about 17 nm. Since first, second and third distances d1, d2, and d3 are respectively within the first, second and third predetermined ranges, interference pattern I11 is marked as a qualified interference pattern, and object A1 corresponding to interference pattern I11 is classified as a qualified object.

A topography structure of curved surface A13 of object A1 is restructured according to the curve diagram of FIG. 6B. Point P1 is a center of concentric circles C11, and a point P1 having a coordinate (X, Y) is positioned at a proper position in the curve diagram.

In FIG. 6B, the coordinate of point P1 is about (170, 10). Point P2 has a coordinate (X+X1, Y+Y1), and the X1 is the value of first distance d1, and the Y1 is a value of the wavelength of the light beam emitted by light source 10. Point P3 has a coordinate (X+X1+X2, Y+2*Y1), and the X2 is the value of second distance d2. Point P4 has a coordinate (X+X1+X2+X3, Y+3*Y1), and the X3 is the value of third distance d3.

Therefore, a curved line CV is drawn in the curve diagram of FIG. 6B according to points P1, P2, P3, P4, and P5. Curved line CV corresponds to the topography structure of curved surface A13 of object A1 as shown in FIG. 3B. Namely, the topography structure of curved surface A13 of object A1 is restructured, and the quality of object A1 may be easily determined according to curved line CV.

Figures 7A, 7B:
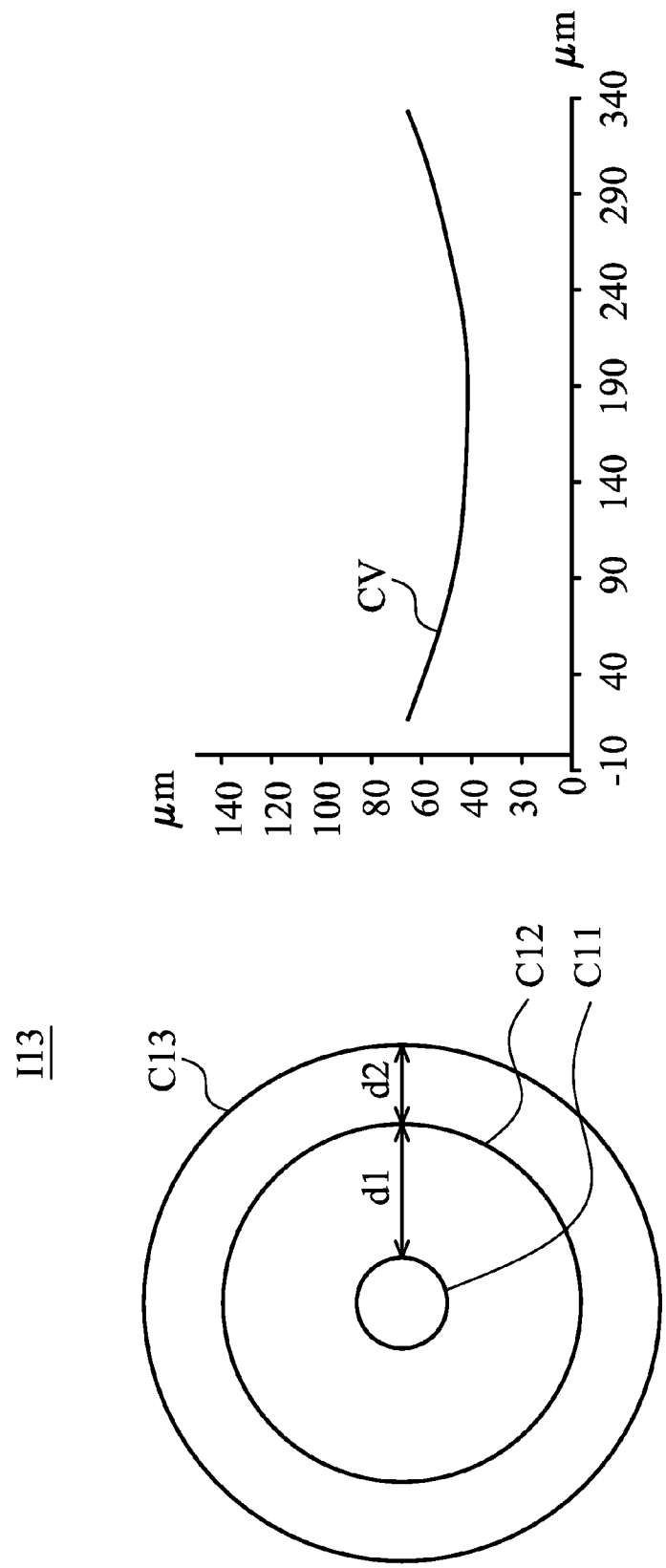
FIG. 7A is a top view of an interference pattern in accordance with some embodiments of the disclosure.
FIG. 7B is a curve diagram corresponding to the interference pattern in FIG. 7A.

In some embodiments, as shown in FIGS. 7A and 7B, interference pattern I13 has three concentric circles C11, C12, and C13. First distance d1 between concentric circles C11 and C12 is about 100 um, which exceeds the first predetermined range. Second distance d2 between concentric circles C12 and C13 is about 50 um, which exceeds the second predetermined range. Therefore, interference pattern I13 is marked as a defect interference pattern, and the object A1 corresponding to interference pattern I13 is classified as a defect object.

Further, since interference pattern I13 has less concentric circles C1 than qualified interference pattern I11, curved line CV of interference pattern I13 is flatter than curved line CV of interference pattern I11. Therefore, the quality of interference pattern I1 is easily determined by the number of concentric circles C1 of the interference pattern I1. For example, if the number of concentric circles C1 is not equal to or less than the predetermined number, such as 5, inspection image F11 corresponding to interference pattern I13 is classified as a defect image, and object A1 corresponding to interference pattern I13 is classified as a defect object.

In addition, if the number of concentric circles C1 is equal to a predetermined number, inspection image F11 corresponding to interference pattern I11 as shown in FIG. 6A may be classified as a qualified image, and object A1 corresponding to interference pattern I11 may be classified as a qualified object.

Figure 8B:
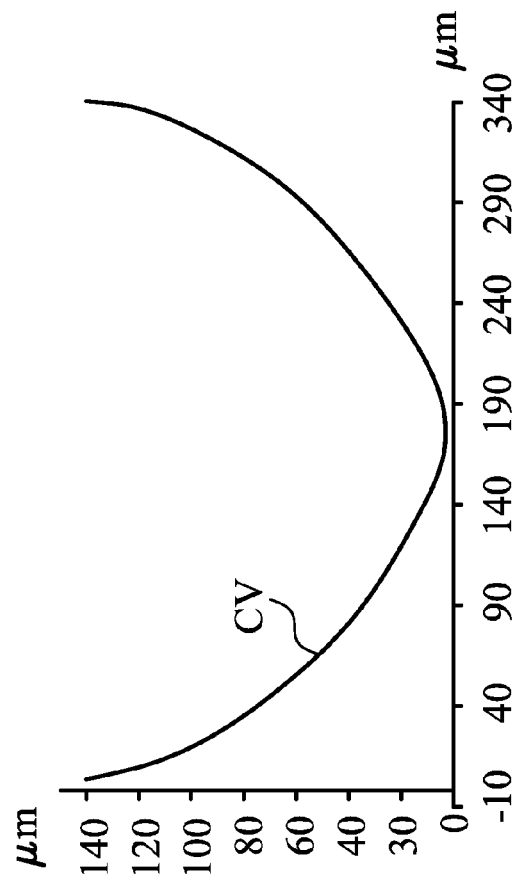
FIG. 8B is a curve diagram corresponding to the interference pattern in FIG. 8A.
Figure 8A:
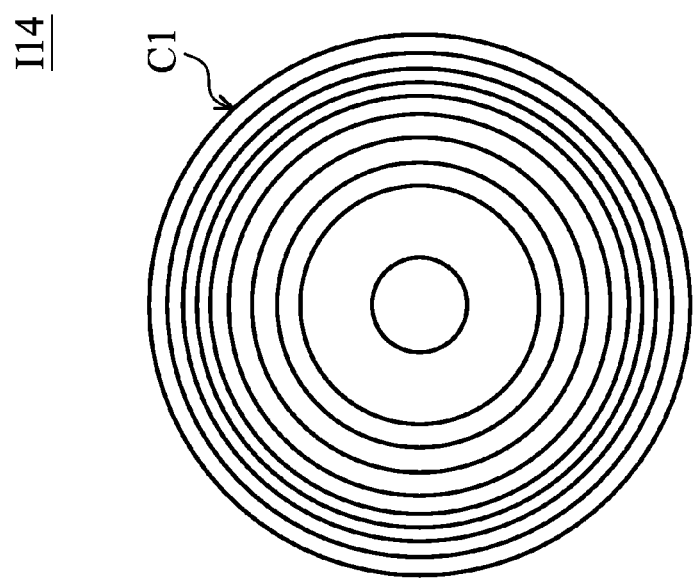
FIG. 8A is a top view of an interference pattern in accordance with some embodiments of the disclosure.

FIG. 8A is a top view of an interference pattern I14 in accordance with some embodiments of the disclosure. FIG. 8B is a curve diagram corresponding to interference pattern I14 in FIG. 8A. In some embodiments, interference pattern I14 has more concentric circles C1 than qualified interference pattern I11, and curved line CV of interference pattern I14 is more curved than curved line CV of interference pattern I11. Since the number of concentric circles C1 is not equal to or greater than the predetermined number, inspection image F11 corresponding to interference pattern I14 is classified as a defect image, and object A1 corresponding to interference pattern I14 is classified as a defect object.

Figure 9B:
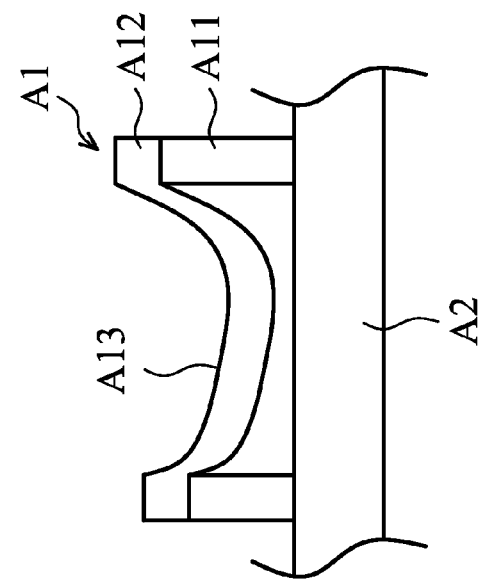
FIG. 9B is a cross-sectional view of an object and a substrate corresponding to the interference pattern in FIG. 9A.
Figure 9A:
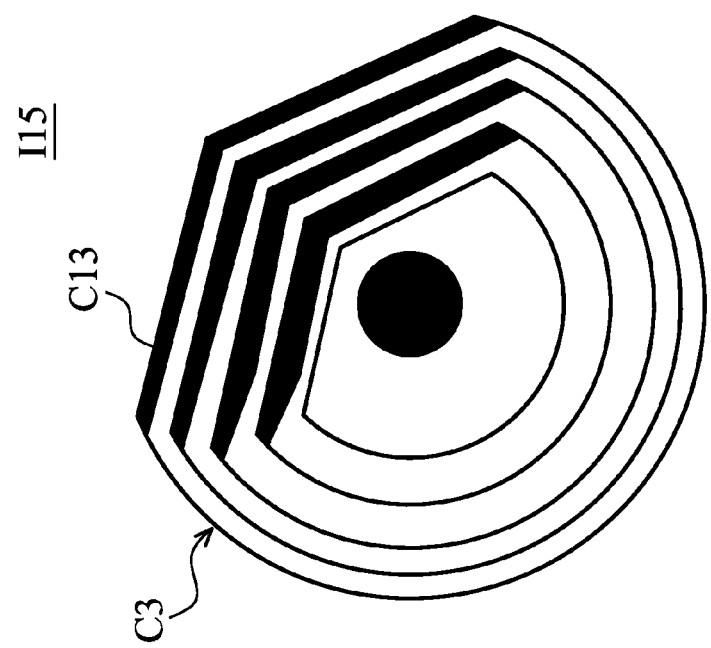
FIG. 9A is a top view of an interference pattern in accordance with some embodiments of the disclosure.

FIG. 9A is a top view of an interference pattern I15 in accordance with some embodiments of the disclosure. FIG. 9B is a cross-sectional view of object A1 and substrate A2 corresponding to interference pattern I15 in FIG. 9A. In some embodiments, interference pattern I15 has rings C3 with at least one flat segment C31, and one side of surface A13 is more inclined than the other side. Therefore, inspection image F11 corresponding to interference pattern I15 is classified as a defect image, and object A1 corresponding to interference pattern I15 is classified as a defect object.

Figure 10B:
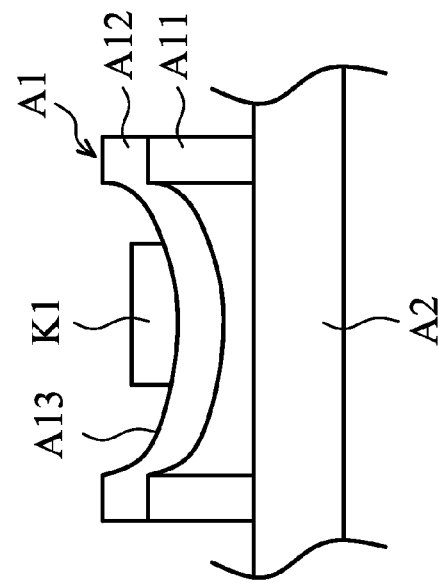
FIG. 10B is a cross-sectional view of an object and a substrate corresponding to the interference pattern in FIG. 10A.
Figure 10A:
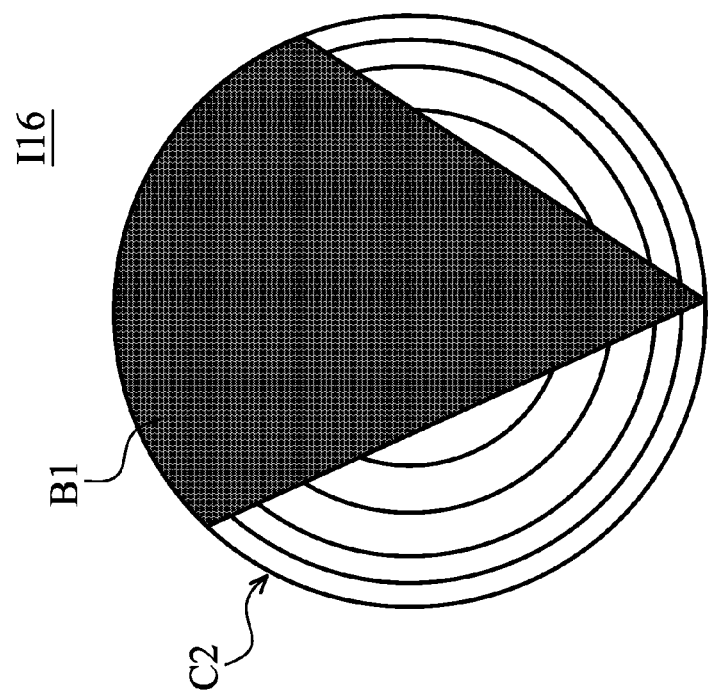
FIG. 10A is a top view of an interference pattern in accordance with some embodiments of the disclosure.

FIG. 10A is a top view of an interference pattern I16 in accordance with some embodiments of the disclosure. FIG. 10B is a cross-sectional view of object A1 and substrate A2 corresponding to interference pattern I16 in FIG. 10A. In some embodiments, interference pattern I16 has a mass area and uncompleted concentric circles C2. Here, a particle K1 may have fallen down on surface A2. Therefore, inspection image F11 corresponding to interference pattern I16 is classified as a defect image, and object A1 corresponding to interference pattern I16 is classified as a defect object.

Figure 11C:
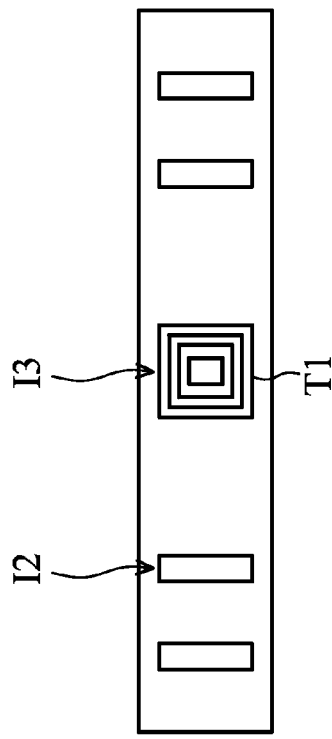
FIG. 11C illustrates interference patterns corresponding to the object in accordance with some embodiments of the disclosure.
Figure 11A:
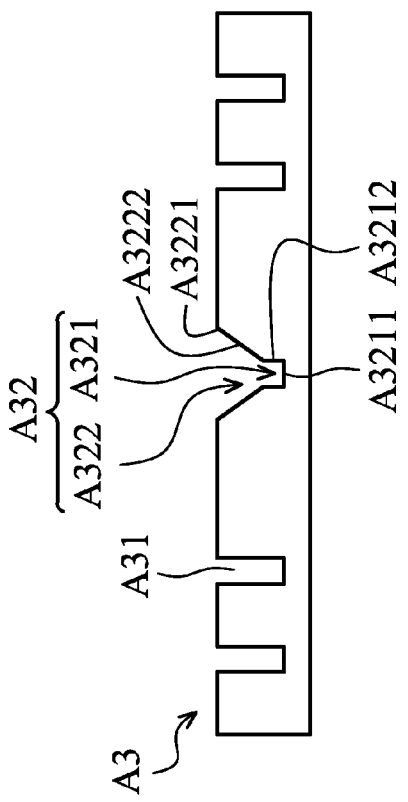
FIG. 11A is a cross-sectional view of an object in accordance with some embodiments of the disclosure.
Figure 11B:
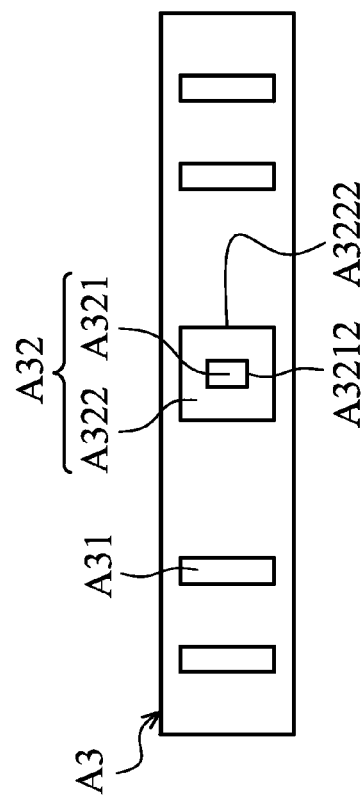
FIG. 11B is a top view of the object in accordance with some embodiments of the disclosure.

In some embodiments, the optical inspection system 1 and optical inspection method is applied to variety of objects with a variety surfaces. FIG. 11A is a cross-sectional view of an object A3 in accordance with some embodiments. FIG. 11B is a top view of object A3 in accordance with some embodiments. FIG. 11C illustrates interference patterns 12 and 13 corresponding to object A3 in accordance with some embodiments. Object A3 has rectangle grooves A31 and grooves A32. Interference pattern 12 corresponding to groove A31 is rectangle.

Rectangle grooves A31 has a bottom portion A321 and a top portion A322. Bottom portion A321 is a cuboid with a rectangle bottom surface A3211 and a rectangle opening A3212. Top portion A322 has a rectangle opening A3221 and an inclined surface A3222 connected with rectangle opening A3212 and A3221. Interference pattern 13 corresponding to interference pattern 12 has concentric rectangle T1.

Embodiments of mechanisms for an optical inspection system are provided. The optical inspection system has a simplification structure, and therefore, the difficulty of the manufacturing and the manufacturing cost of the optical inspection system are decreased. An interference pattern of an object is obtained quickly and easily by the optical inspection system. If the object has defect, the interference pattern of the object is significant difference from a qualified interference pattern. Therefore, the determination of the object whether having defect is easier.

In some embodiments, an optical inspection system for inspecting an object is provided. The optical inspection system includes a light source emitting a coherent beam having a first width, and a beam expander increasing the first width to a second width. The optical inspection system also includes a polaroid module adjacent to the beam expander and polarizing the coherent beam. The object generates an inspection beam with an interference pattern by reflecting the polarized coherent beam. The optical inspection system further includes an image module capturing the inspection beam.

In some embodiments, an optical inspection method is provided. The optical inspection method includes emitting a coherent beam from a light source. The method further includes increasing a width of the coherent beam by a beam expander. The method further includes polarizing the coherent beam by a polaroid module. The method further includes reflecting the polarized coherent beam by the object to generate an inspection beam with an interference pattern. The method further includes capturing the inspection beam by an image module.

In some embodiments, an optical inspection method is provided. The optical inspection method includes emitting a polarized coherent beam to an object, and generating an inspection beam with an interference pattern according to a surface of an object. The object generates the inspection beam by reflecting the polarized coherent beam. The method further includes capturing the inspection beam. The method further includes providing an inspection image with the interference pattern. The method further includes detecting the inspection image. The method further includes classifying the object as a defect object when the inspection image corresponding to the object excludes a plurality of concentric circles or includes the concentric circles having a distance between two adjacent concentric circles which exceed a predetermined range.

Although embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An optical inspection system for inspecting an object, comprising:
    a light source emitting a coherent beam having a first width;
    a beam expander increasing the first width to a second width;
    a polaroid module, adjacent to the beam expander, polarizing the coherent beam, wherein the object generates an inspection beam with an interference pattern by reflecting the polarized coherent beam; and
    an image module, capturing the inspection beam, generating an image signal according to the interference pattern;
    wherein the object is classified as a defect object when an inspection image corresponding to the object and the image signal excludes a plurality of concentric circles or includes the concentric circles having a distance between two adjacent concentric circles which exceed a predetermined range.

2. The optical inspection system as claimed in claim 1, wherein the light source is a laser emitting device, and the coherent beam is a laser beam.

3. The optical inspection system as claimed in claim 1, wherein the light source, the beam expander, the polaroid module, and the half-reflect mirror are arranged along a first axis and the half-reflect mirror, and the image module are arranged along a second axis in sequence, wherein the first axis is perpendicular to the second axis.

4. The optical inspection system as claimed in claim 1, wherein the beam expander comprises a first lens and a second lens arranged along a first axis in sequence, wherein the first lens is adjacent to the light source, and the second lens is adjacent to the polaroid module.

5. The optical inspection system as claimed in claim 4, wherein the first lens is a symmetrical double convex lens, and the second lens is a symmetrical biconcave lens.

6. The optical inspection system as claimed in claim 4, wherein the beam expander further comprises a third lens and a fourth lens, wherein the first lens, the third lens, the fourth lens, and the second lens are arranged along the first axis in sequence.

7. The optical inspection system as claimed in claim 1, wherein the polarized coherent beam emitted to the object and the inspection beam reflected by object are transmitted along the same axis.

8. The optical inspection system as claimed in claim 1, further comprising a half-reflect mirror reflecting the polarized coherent beam to the object.

9. The optical inspection system as claimed in claim 1, wherein the object has a curved surface, and the interference pattern corresponds to the curved surface.

10. The optical inspection system as claimed in claim 1, wherein the interference pattern has a plurality of concentric circles.

11. The optical inspection system as claimed in claim 1, wherein the image module comprises a camera capturing the inspection beam.

12. The optical inspection system as claimed in claim 11, further comprising:
    a processes module, communicated with the image module, generating an inspection signal according to the image signal; and
    a display, electrically connected with the processes module, displaying the inspection image according to the inspection signal.

13. An optical inspection method, comprising:
    emitting a coherent beam from a light source;
    increasing a width of the coherent beam by a beam expander;
    polarizing the coherent beam by a polaroid module;
    reflecting the polarized coherent beam by an object to generate an inspection beam with an interference pattern;
    capturing the inspection beam by an image module;
    detecting an inspection image with the interference pattern; and
    classifying the object as a defect object when the inspection image corresponding to the object excludes a plurality of concentric circles or includes the concentric circles having a distance between two adjacent concentric circles which exceed a predetermined range.

14. The optical inspection method as claimed in claim 13, further comprising reflecting the polarized coherent beam to the object by a half-reflect mirror.

15. The optical inspection method as claimed in claim 13, further comprising: classifying the object as a qualified object when the inspection image corresponding to the object includes the concentric circles, and a number of the concentric circles is equal to a predetermined number.

16. The optical inspection method as claimed in claim 13, further comprising: drawing a line corresponding to the surface of the object according the distance and the wavelength of the coherent beam when the inspection image includes the concentric circles.

17. An optical inspection method, comprising:
    emitting a polarized coherent beam to an object, and generating an inspection beam with an interference pattern according to a surface of an object, wherein the object generates the inspection beam by reflecting the polarized coherent beam;
    capturing the inspection beam;
    providing an inspection image with the interference pattern;
    detecting the inspection image; and
    classifying the object as a defect object when the inspection image corresponding to the object excludes a plurality of concentric circles or includes the concentric circles having a distance between two adjacent concentric circles which exceed a predetermined range.

18. The optical inspection method as claimed in claim 17, further comprising: classifying the object as a qualified object when the inspection image corresponding to the object includes the concentric circles, and a number of the concentric circles is equal to a predetermined number.

19. The optical inspection method as claimed in claim 17, further comprising: drawing a curved line corresponding to the surface of an object according the distance and the wavelength of the polarized coherent beam when the inspection image includes the concentric circles.

* * * * *